United States Patent
Kemp et al.

Patent Number: 5,161,681
Date of Patent: Nov. 10, 1992

[54] SAFETY CONTAINER FOR HYPODERMIC SYRINGES

[76] Inventors: David R. Kemp, 2213 Richmond Rd., Paradise, Calif. 95969; Donald J. Evans, P.O. Box 418, Forest Ranch, Calif. 95942

[21] Appl. No.: 697,730

[22] Filed: May 3, 1991

Related U.S. Application Data

[63] Continuation-in-part of Ser. No. 342,553, Apr. 24, 1989, abandoned.

[51] Int. Cl.⁵ ............... A61L 2/16; B65F 1/00
[52] U.S. Cl. .................. 206/210; 206/364; 206/493
[58] Field of Search .......... 206/363, 364, 365, 366, 206/367, 210, 493, 534, 459

[56] References Cited

U.S. PATENT DOCUMENTS

| | | | |
|---|---|---|---|
| 426,400 | 4/1890 | Tagliabue | 206/306 |
| 585,007 | 6/1897 | Rambaud | 206/367 |
| 1,280,687 | 10/1918 | Dudley | 206/210 |
| 1,421,219 | 6/1922 | Harmon | 206/459 X |
| 1,694,768 | 12/1928 | Cook | 604/263 |
| 1,838,825 | 12/1931 | Goldstein | 206/210 |
| 2,400,722 | 5/1946 | Swan | 206/210 |
| 2,972,991 | 2/1961 | Burke | 604/110 |
| 3,270,743 | 9/1966 | Gingras | 604/192 |
| 3,329,146 | 7/1967 | Waldman, Jr. | 604/192 |
| 3,336,924 | 8/1967 | Sarnoff et al. | 206/364 X |
| 3,416,657 | 12/1968 | Sorensen, Jr. et al. | 206/364 X |
| 3,637,072 | 1/1972 | Narusawa et al. | 206/365 X |
| 4,098,577 | 6/1978 | Halpern | 206/364 X |
| 4,623,336 | 11/1986 | Pedicano | 604/192 |
| 4,735,311 | 4/1988 | Lowe et al. | 206/365 |
| 4,848,569 | 7/1989 | Leishman | 206/366 X |
| 4,877,132 | 10/1989 | Malris et al. | 206/364 |
| 4,878,903 | 11/1989 | Mueller | 206/364 X |
| 4,919,264 | 4/1990 | Shinall | 206/210 |
| 4,936,449 | 6/1990 | Conard et al. | 206/366 |
| 5,024,326 | 6/1991 | Sandel et al. | 206/364 X |
| 5,038,929 | 8/1991 | Kubofcik | 206/364 X |

FOREIGN PATENT DOCUMENTS 610245 9/1926 France ............... 206/364

*Primary Examiner*—Paul T. Sewell
*Assistant Examiner*—Jacob K. Ackun, Jr.

[57] ABSTRACT

A safety container for storing and transporting a hypodermic syringe with attached needle, wherein the container is comprised of an elongated transparent plastic tube having a closed end and an oppositely disposed open end. The open end is fitted with a removable lid. The closed end of tube contains a rubbery pad into which the needle point of the syringe is embedded. The resilient, self-sealing rubbery pad frictionally holds the needle and syringe secure, and seals the lumen of the needle to prevent leakage of fluid from the needle or syringe. At least one end of the container has flat edges to prevent rolling of the container when positioned horizontally or when in a moving vehicle.

1 Claim, 7 Drawing Sheets

SAFETY CONTAINER FOR HYPODERMIC SYRINGES

CROSS-REFERENCES TO RELATED APPLICATIONS

This is a continuation-in-part of applications Ser. No. 342,553, filed Apr. 24, 1989, now abandoned.

BACKGROUND OF THE INVENTION

1. Field of the Invention

This invention relates to containers usefull for safe transportation of filled and partially filled hypodermic syringes. The present invention is particularly directed towards a container sized for field service and structured with protective features allowing filled and partially filled hypodermic syringes to be packaged and transported to a laboratory. The design of the invention also allows filled and partially filled hypodermic syringes to be packaged for safe storage. This is particularly important for police officers who must transport used hypodermic syringes from the field to a laboratory and for storing the contents of used hypodermic syringes for evidence and for presentation as evidence in court.

2. Description of the Prior Art

From a patent search, it is evident that containers for safe storage of delicate medical equipment were considered essential quite a few years ago. for example, in U.S. Pat. No. 426,400 issued to C. J. Taglabue on Apr. 22, 1890, a tubular thermometer case is illustrated. Elastic pad closure members are used as end stops to protect the enclosed thermometer.

In another early patent, U.S. Pat. No. 585,007, granted to G. G. Rambaud on Jun. 22, 1897, a vaccine point protector is shown. The use of paraffin to seal in an end stopper is described in this patent.

The Cook patent dated Dec. 11, 1928, U.S. Pat. No. 1,694,768, describes and illustrates a tubular container sealed at one end and closed with a stopper at the other end. The purpose of the invention is to provide safety from contamination for hypodermic needles prior to injections. The needle only is contained and not the syringe.

G. K. Burke shows a disposable syringe with a needle guard. His patent was issued Feb. 28, 1961, U.S. Pat. No. 2,972,991. A cotton filler is used adjacent an opening in the tip of the needle guard. The cotton filler is used as a filter in this application.

U.S. Pat. No. 3,270,743, granted to P. Gingras on Sep. 6, 1966, shows a syringe container useful for keeping the needle sterilized prior to use. The end of the needle is inserted into a cotton pad which has been impregnated with an antiseptic liquid.

A patent issued to L. F. Waldman, Jr., on Jul. 4, 1967, U.S. Pat. No. 3,329,146, illustrates and describes a syringe needle container. The container is designed just to sheath the needle and provides a quick release for attaching the needle to a syringe.

In the "Disposable Safety Needle Sheath" shown in U.S. Pat. No. 4,623,336, a needle sized container is affixed at a receiving end with a capped funnel. The device is primarily designed for handling safety during the disposal of contaminated materials.

The Conard et al patent issued Jun. 26, 1990, U.S. Pat. No. 4,936,449, teaches a disposable sharps retaining and disposal device. This device includes a block of absorbent polystyrene foam for penetration by and for frictionally holding disposable hypodermic syringes, scalpels and other sharps within a lidded container. The polystyrene foam of Conard's device would not sufficiently prevent leakage of the syringe contents due to the porous nature of the material utilized to hold the sharps, and in fact Conard describes the polystyrene foam as being absorbent so that liquid contaminants, such as blood and other fluids with which the sharps may be contaminated, are less likely to leak from the block. Since the polystyrene block of Conard's device is absorbent, and is intended to be absorbent by admission of Conard, it cannot seal a needle tip and prevent leakage of the syringe or needle contents.

None of the previously mentioned past art patents teach a container for safely containing and restraining against movement a used hypodermic syringe with the needle tip sealed to prevent leakage of the syringe contents. Our device is directed towards protection of the people handling and transporting a used syringe and also the protection of the syringe, and specifically its contents, for later examination and identification. The current method of collecting hypodermic syringes by low enforcement personnel for evidence in legal prosecution often merely includes placement of the syringe with needle into a plastic bag. Since the syringes and their contents are often used as evidence in a court case, it is desirable to attempt to save even the last minuscule amount of fluid left in a used syringe for laboratory analysis. None of the devices of the past art are structurally capable of providing these qualities and therefore could not function as our device or provide the benefits thereof.

SUMMARY OF THE INVENTION

Our safety container for a syringe is comprised of an elongated, puncture resistant tube, preferably made of transparent plastic. The tube is of sufficient open interior diameter and length to completely contain at least a single hypodermic syringe with needle, even with the plunger of the syringe extended. One end of tube, designated the bottom end, is permanently enclosed with a puncture resistant bottom end cap or an equivalency thereof, which contains a pad of fluid impervious rubbery material retained in communication with the open interior of the tube. The oppositely disposed end of the tube, designated the top end, is fitted with a removable lid, end cap or an equivalency thereof to prevent the inadvertent escape of a contained syringe.

The soft rubbery material or pad in the bottom end of the tube possesses self-sealing resilient characteristics to allow the needle point of a syringe to penetrate in any location on the exposed surface of the pad. When a needle penetrates the soft rubbery material, due to the resilient nature of the material, the needle is frictionally retained rather securely by frictional adhesion, and thus the syringe is retrained from excessive movement within the container. Securing the needle and syringe prevents the plunger end of the syringe from falling against the interior of the upper lid, depressing the plunger, and possibly forcing the ejection of some of the syringe or needle contents, or possibly forcing the upper lid off allowing the syringe to fall out of the container.

Since the rubbery material constantly attempts to re-seal itself by way of its resiliency, the rubbery material applies pressure against the embedded needle tip and holds the needle mechanically secure. Additionally, since the rubbery material of the pad is fluid impervious, and by way of resiliency grips the needle point securely, the retained open tip or lumen of the needle is sealed fluid tight, preventing fluid which may be within the needle or syringe from leaking from the needle or syringe.

Additionally, an anti-roll end cap having large flat surfaces is placed over the exterior of the bottom end cap of the syringe container to prevent the container from rolling when placed lying horizontally on an uneven surface or when being transported in a moving vehicle as is so often the case. The opposite or top end of the tube of the container is fitted with the resealable lid, an outer lip of which is also desirably shaped to possess flat surfaces to assist in preventing rolling.

The plastic material used to manufacture the tube, the bottom end cap and the resealable top lid are all of sufficient strength and hardness to prevent penetration by the needle of the syringe and prevent collapse of the tube from moderate accidental compression.

One primary object of this invention is to provide a safe and secure container for transporting and storing used hypodermic syringes such as those found at clandestine drug labs or other crime scenes for example. The container itself is structured to prevent penetration by the needle tip to prevent accidental puncture of the human handler. The container also helps protect the syringe from being crushed, which could expose the handler to the syringe contents. The transparent sidewall allows the syringe and attached needle to be visually examined without removing the top cap or the syringe which would further expose the handler to potential contamination.

A further advantage of our invention is that the syringe can be inserted into the container with one hand, thereby eliminating the possibility of inadvertently puncturing one hand holding the container as the syringe is inserted into the tube with the other hand. This safe one-handed insertion of the syringe with needle is made possible primarily by the anti-roll features, by the transparent tube, and by the characteristics of the soft rubbery pad in combination.

Other advantages of our invention such as inexpensive manufacturing of our syringe container and safe convenient use thereof will be understood with a reading of the remaining specification and examination of the accompanying numbered drawings.

DESCRIPTION OF THE PREFERRED EMBODIMENT

Figure 6:
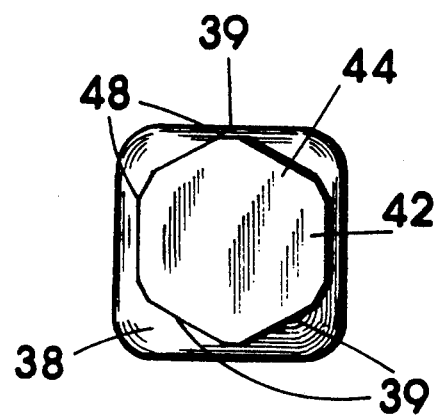
FIG. 6 is a top end view of our assembled safety container.
Figure 10:
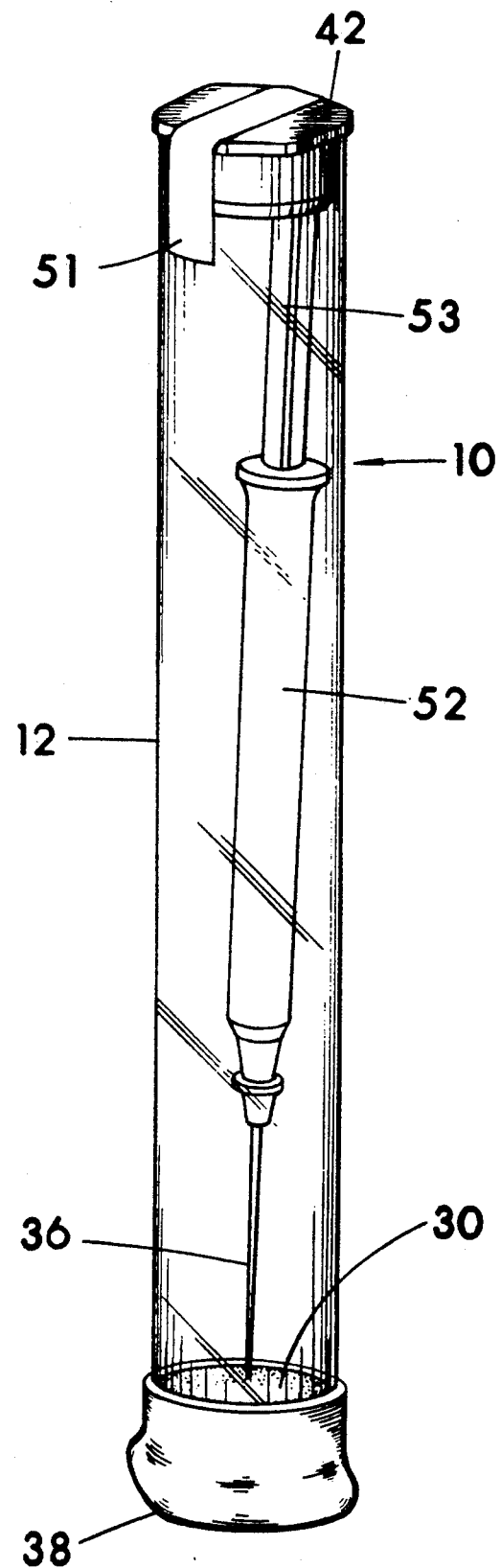
FIG. 10 is a perspective view illustrating our safety container retaining a hypodermic syringe with needle, with the plunger of the syringe in an extended position.

Referring now to the drawings in general where a preferred embodiment of our safety container 10 is shown in several stages of assembly and in use for example. Safety container 10 is comprised of an elongated right cylindrically shaped tube 12 having an open interior extending from one end to the other oppositely disposed end of tube 12. The open interior of tube 12 is sized diametrically and in length to be able to contain a syringe 52 having an attached needle 36, even with the plunger 53 of the syringe 52 fully extended as shown in FIG. 10. Tube 12 is manufactured of a semi-rigid, generally shatter and puncture resistant transparent plastic. Clear or transparent PVC thermoplastic or cellulose Acetate are suitable materials from which to manufacture tube 12, and tube 12 may be inexpensively and effectively formed in quantity by extrusion of the plastic. Tube 12 has two oppositely disposed open ends 14 A and 14 B, with end 14 A positioned at waht is considered the bottom end of tube 12, and 14 B at what is considered the top end of tube 12. Open end 14 B, at the top end of tube 12, may be temporarily closed with a resealable cap or lid 42 utilizing an interference fit with tube 12. Resealable lid 42 is comprised of a flat plate 44 and a short annular sidewall 46. Annular sidewall 46 is sized to fit snugly within open end 14 B. An overhanding lip 48 which is an extension of plate 44 is roughly hexagon in shape as shown in FIG. 6, having flattened edges 39 positioned outward beyond the external diameter of tube 12, which help to prevent container 10 from rolling on an uneven surface. Lip 48 also provides a grasping edge for the user for easy removal of resealable lid 42. The rim of annular sidewall 46 contains an inward beveled edge 50 for easily starting and guiding of resealable lid 42 into open end 14 B. Resealable lid 42 is manually removable from end 14 B and tube 12 to allow the removal or insertion of a syringe 52 with needle 36 through open end 14 B into the open interior of tube 12, at which time lid 42 may be repositioned and again affixed within open end 14 B where it is frictionally retained based on an interference fit. A peel and stick glue backed pressure sensitive label 51 may be applied across the top exterior surface of lid 42 and to tube 12 for an extra secure affixment of lid 42 when containing a syringe 52 if desired. Label 51 would be supplied loose within tube 12 when purchased, and after a syringe 52 has been inserted into tube 12, label 51 may be written on to identify the container contents and the location where the syringe was found, or the evidence or case number. The label 51 may then be utilized as shown in FIG. 10 to seal the container 10 tamper resistant, and as an identifying label. With our invention, lid 42 properly placed within end 14 B of tube 12 does provide a fluid tight seal, but this is not seen to be critical. The described lid 42 which fits into end 14 B of tube 12 is a relatively inexpensive capping arrangement, but could be modified to include cooperative threads on the lid and tube 12, or possibly a hinge, however, these alternative arrangements would most likely cost additional money to manufacture, and are not currently seen to be necessary.

Open end 14 A is permanently closed with a short cylindrical bottom end cap 16. Bottom end cap 16 is comprised of a flat annular plate 18 with a short annular sidewall 20 which forms a shallow interior enclosure 22. Annular plate 18 extends beyond sidewall 20 and forms a narrow flange 24 which serves as a shoulder stop to prevent bottom end cap 16 from being inserted too far into open end 14 A. Insertion of bottom end cap 16 into open end 14 A is made easier with the addition of a inward bevel 26 on the upper edge of sidewall 20. The diameter of sidewall 20 of bottom end cap 16 is sized for an interference fit into open end 14 A of tube 12, creating a snug and generally fluid tight fit which initially retains cap 16 in place by friction. Bottom end cap 16 is permanently adhered within end 14 A of tube 12 with the use of adhesives 28 or with sonic bonding or any other suitable permanent method. Bottom end cap 16 is made of a material and material thickness which is puncture resistant, at least puncture resistant to the needle 36 of a syringe 52. Polyethylene, in a substantially rigid form is one suitable plastic material which may be used as the material to make bottom end cap 16, and plastic injection molding is a suitable manufacturing method to make bottom end cap 16 from plastic.

Figure 1:
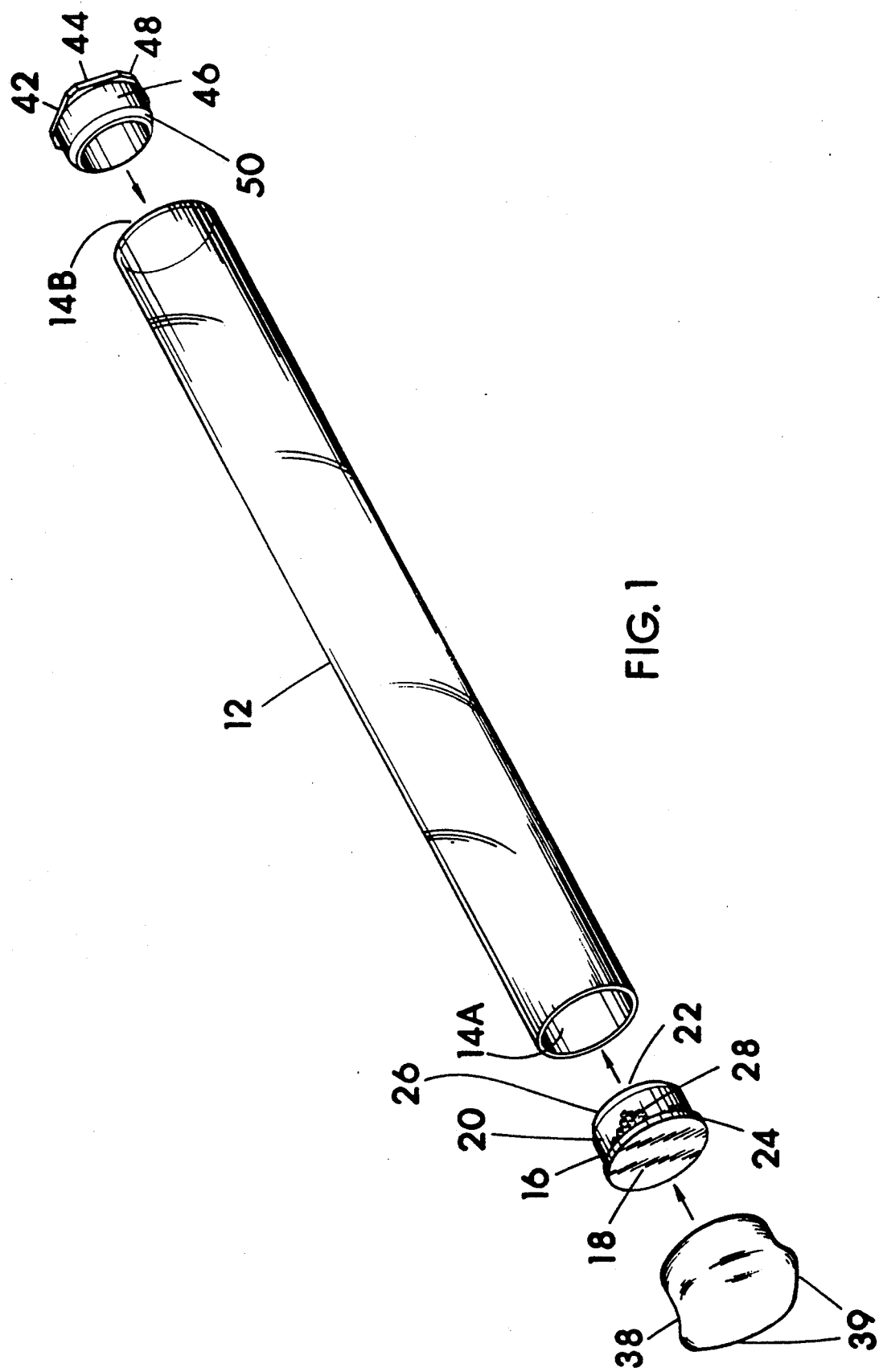
FIG. 1 is an exploded perspective view of our preferred embodiment of safety container for a syringe with needle.
Figure 2:
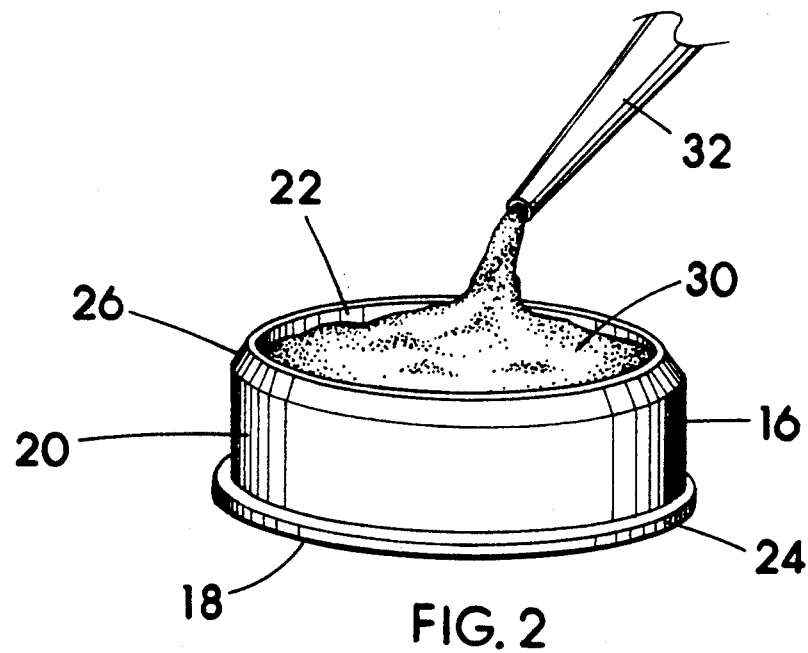
FIG. 2. is a perspective view of the bottom end cap illustrating one method of installation of the rubbery material or pad, where the rubbery pad material may be initially applied as a fluid and air cured.
Figure 3:
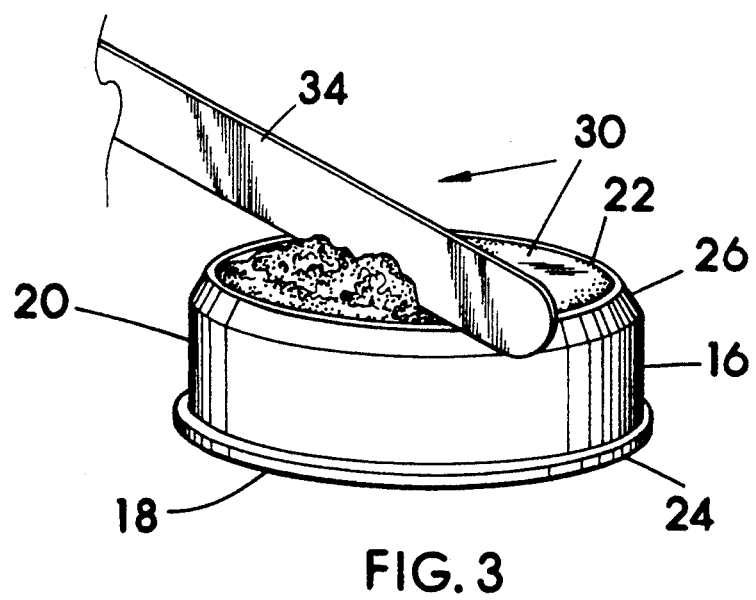
FIG. 3 is a perspective view of the bottom end cap with the rubbery pad installed, still in the fluid stage, illustrating one method of removing and leveling excess material in the bottom end cap.
Figure 4:
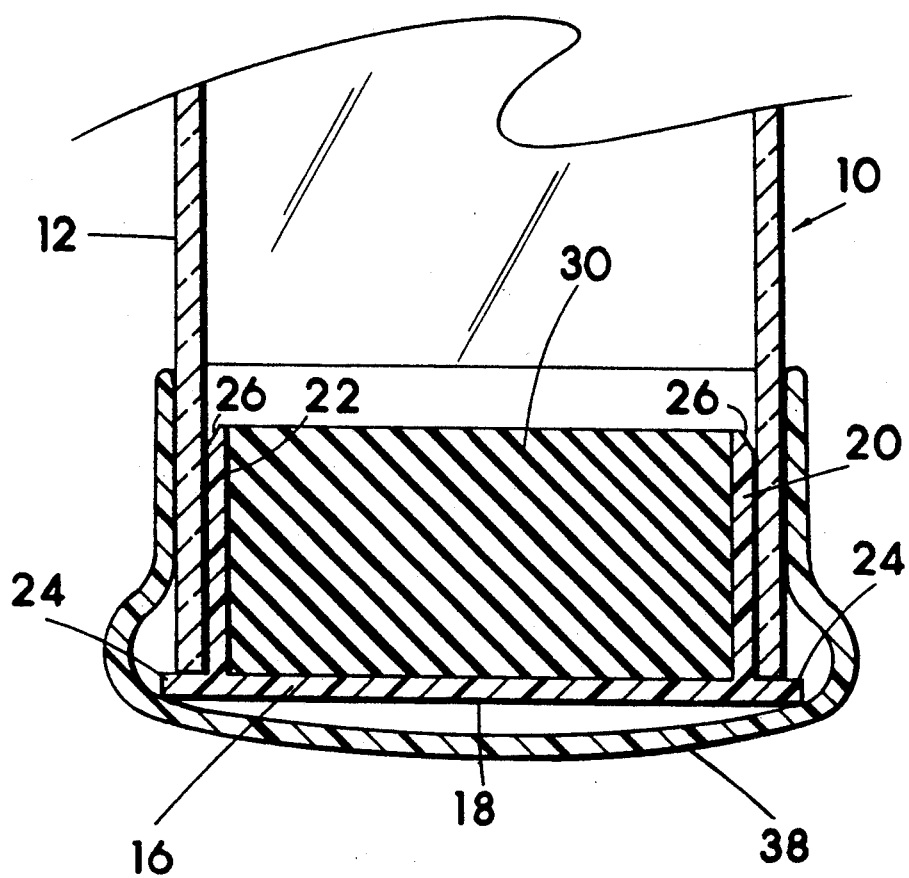
FIG. 4 is an enlarged cross-sectional view of the bottom end of our assembled safety container.
Figure 5:
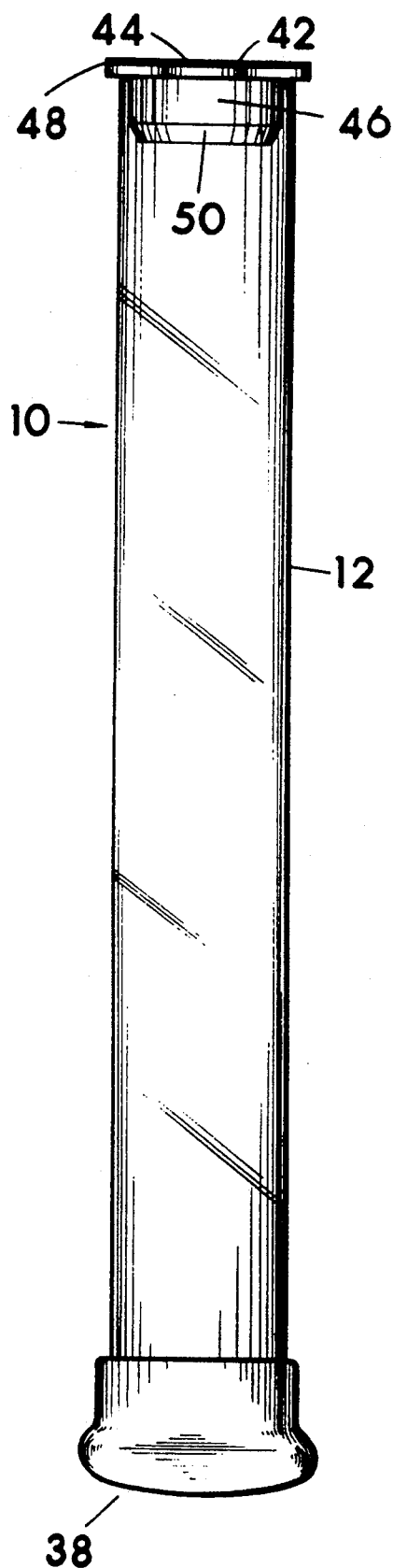
FIG. 5 is a side view of our assembled safety container.
Figure 11:
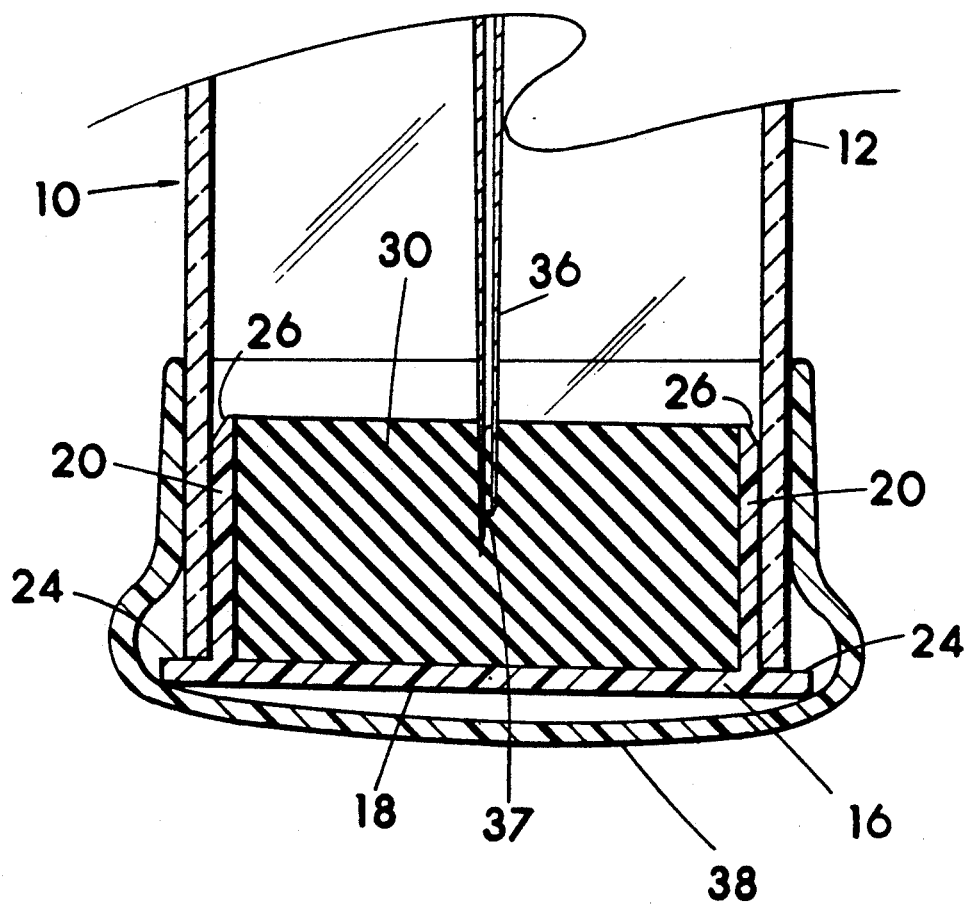
FIG. 11 is an enlarged cross-sectional side view of the bottom end of our safety container illustrating the tip of the needle embedded into the rubbery pad, and the lumen of the needle embedded in, and sealed fluid tight by the rubbery pad.

The shallow interior enclosure 22 of bottom end cap 16 serves to house a rubbery pad 30. Rubbery pad 30 is a soft, pliable, resilient, self-sealing, fluid impervious material such as a silicone rubber or silicone rubber sealant. Although rubbery pad 30 could be die cut in rounds from a solid panel of cured silicone rubber material, and either adhesively affixed into interior enclosure 22 or affixed stationary by way of an interference fit or both, rubbery pad 30 is preferably injected into interior enclosure 22 in a liquid state, shown in FIG. 2 being ejected through nozzle 32. When injected in a liquid state, the silicone rubber provides an adhesive quality and adheres itself to the interior of enclosure 22. After injecting liquid the silicone rubber into enclosure 22, any excess silicone rubber is removed with a straight edge blade 34, as shown in FIG. 3, and left to air cure. Providing a flat level surface to the rubbery pad 30 will help prevent deflection of needle 36 when inserted, and also helps provide a neater appearance. When fully cured, rubbery pad 30 should be relatively chemically inert for accurate future testing of fluids contained within a needle 36 which had been inserted into rubbery pad 30. With bottom end cap 16 inserted into open end 14 A, rubbery pad 30 is positioned between end cap 16 and the open interior of tube 12. Rubbery pad 30 within bottom end cap 16 is about a centimeter in thickness, this being a depth to allow the point of a needle 36 to penetrate sufficiently into pad 30, with the maximum penetration depth being determined by the abutment of the point of needle 36 against the interior surface of flat annular plate 18 of bottom end cap 16, with this depth being more than sufficient to allow the lumen 37 of the needle 36 to be completely submerged into the material of rubbery pad 30 and be sealed fluid tight as shown in FIG. 11. The General Electric Co., Silicone Products Div., Section TR84. Waterford, N.Y. 12188 U.S.A. manufactures and sells a silicone rubber sealant under the trade name of "Silicone II", pronounced "silicone two". This fluid impervious product is available in liquid form, cures in air to a rubbery consistency, and has been found to be most suitable as a material from which to make a rubbery pad 30. It should be noted other rubbery caulkings and sealants or sealant adhesives may also function for rubbery pad 30.

Figure 7:
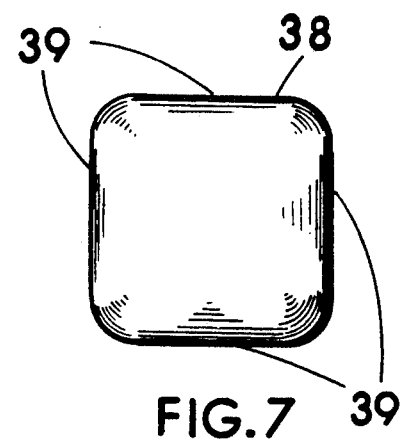
FIG. 7 is a bottom end view of our safety container.

Once bottom end cap 16 is inserted into end 14 A and affixed stationary or permanently to tube 12, anti-roll end cap cover 38 may be affixed over bottom end cap 16. Anti-roll end cap cover 38 is a soft pliable plastic member having an enclosed end and an oppositely disposed open end which is sized for insertion over the exterior of the bottom end of tube 12 and bottom end cap 16. The closed bottom end of anti-roll end cap cover 38 has four flat edges 39, best shown in FIG. 7, which extend outward beyond the major diameter of tube 12, and which help prevent tube 12 from rolling when placed horizontally on a flat or uneven surface. Anti-roll end cap cover 38 is generally affixed to tube 12 with a interference fit since it is quite resilient, but it can also be permanently affixed with adhesives 28.

Figure 9:
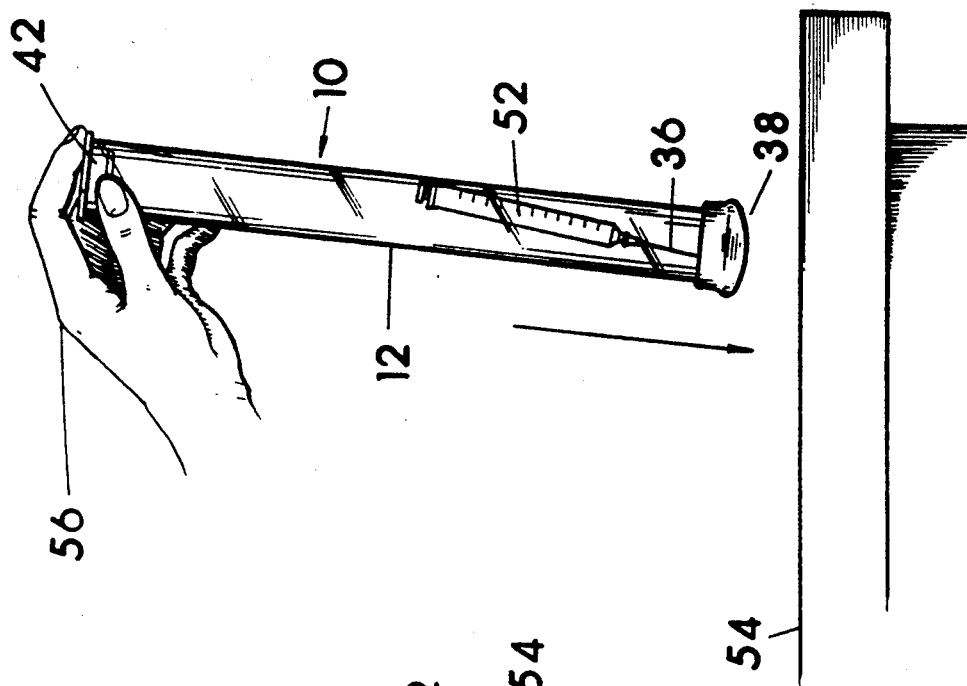
FIG. 9 is an illustration further depicting the inserting of the syringe with needle which includes shaking or taping the bottom end of the container to embed the needle of the syringe into the rubbery pad.
Figure 8:
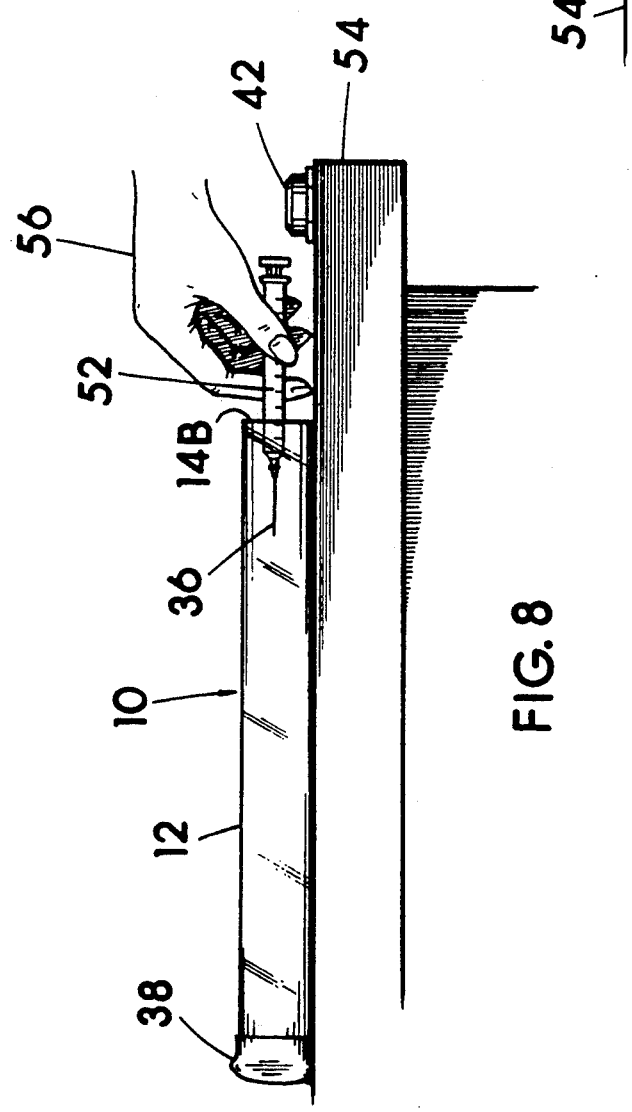
FIG. 8 is an illustration depicting the inserting of a hypodermic syringe with needle into our container, where the container is placed horizontally on a flat surface and prevented from rolling so only one hand is needed to insert the syringe.

The recommended method of inserting syringe 52 with affixed needle 36 into safety container 10 is illustrated in FIGS. 8 and 9. Resealable lid 42 is first manually removed from tube 12, and tube is positioned horizontally on a level surface 54. With one hand 56, the user inserts syringe 52 into open end 14 B of cylindrical tube 12, needle 36 first. The user then picks up tube 12 and replaces resealable lid 42. With one finger over the top of lid 42, tube 12 is then positioned relatively vertically and bottom end cap 16 is tapped on a surface 54 several times, or container 10 is merely forced quickly downward followed by a quick upward jerk, to firmly imbed the tip of needle 36 into rubbery pad 30. Utilizing this insertion method, the user eliminates the chance of accidentally puncturing his hand 56 with needle 36 should syringe 52 accidentally be deflected from entering open end 14 B, as might be the case if the user were holding tube 12 while inserting syringe 52. By tapping the bottom of anti-roll end cap cover 38, the tip of needle 36 penetrates rubbery pad 30 a sufficient depth to engage needle 36 and restrain both needle 36 and syringe 52 against substantial movement within tube 12, and to cover lumen 37 preventing leakage of the contents of needle 36 and syringe 52.

Although we have described our safety container 10 in detail in the specification and specifically detailed it in the drawings, this is for example only. Modifications can be made in our invention without departing from the scope of the invention as defined in our claims.

The embodiments of the invention in which an exclusive property or privilege is claimed are defined as follows:

1. In combination, a safety container and a hypodermic syringe with attached needle, comprising:
    an elongated right cylindrically shaped hollow tube manufacture of shatter and puncture resistant substantially transparent plastic material, said tube having an open interior fully containing said hypodermic syringe with attached needle with a plunger of said hypodermic syringe in an extended position, said tube having a first open end and an oppositely disposed second end, a first closing means on said first open end of said tube closing said open interior at said first open end of said tube, said first closing means being manually movable to permit removal of said hypodermic syringe with attached needle from said open interior of said tube, a second closing means on said second end of said tube, said second closing means structured of puncture resistant material so as to prevent puncturing thereof by said needle of said hypodermic syringe, a soft rubbery pad affixed between said second closing means and said open interior within said tube, said needle of said hypodermic syringe partly inserted into said rubbery pad, said needle and said hypodermic syringe substantially restrained from movement by way of resiliency in said rubbery pad causing frictional adhesion between said rubbery pad and said needle, said needle having a lumen positioned within said rubbery pad, said rubbery pad being of substantially fluid impervious material, said lumen of said needle sealed fluid tight by said resiliency and the fluid impermeability of said rubbery pad, at least one generally flat extending exterior surface affixed on said safety container providing means for generally preventing rolling of said safety container when said safety container is positioned horizontal oriented on a surface, labeling means affixed to said tube for displaying information pertinent to said hypodermic syringe with attached neddle.

* * * * *